United States Patent [19]

Kawasaki et al.

[11] Patent Number: 5,280,107
[45] Date of Patent: Jan. 18, 1994

[54] PROCESS FOR PRODUCING K-CASEIN GLYCOMACROPEPTIDES

[75] Inventors: Yoshihiro Kawasaki, Kawagoe; Shunichi Dosako, Urawa; Masaharu Shimatani, Sayama; Tadashi Idota, Kawagoe, all of Japan

[73] Assignee: Snow Brand Milk Products Co., Ltd., Hokkaido, Japan

[21] Appl. No.: 831,255

[22] Filed: Jan. 17, 1992

[30] Foreign Application Priority Data

Jan. 21, 1991 [JP] Japan .................... 3-19112

[51] Int. Cl.$^5$ .................... C07K 1/00; C07K 15/14
[52] U.S. Cl. .................... 530/361; 530/322; 530/395; 435/68.1
[58] Field of Search .................... 530/395, 361, 322; 435/68.1

[56] References Cited

U.S. PATENT DOCUMENTS

| 3,930,039 | 12/1975 | Kuipers . | |
|---|---|---|---|
| 4,042,576 | 8/1977 | Eustache | 530/322 |
| 4,485,640 | 11/1984 | Roger et al. . | |
| 5,061,622 | 10/1991 | Dosako et al. | 435/68.1 |
| 5,075,424 | 12/1991 | Tanimoto et al. | 530/361 |

Primary Examiner—Howard E. Schain
Assistant Examiner—P. Touzeau
Attorney, Agent, or Firm—Browdy and Neimark

[57] ABSTRACT

The present invention provides a process for producing κ-casein glycomacropeptides which comprises contacting milk raw materials containing κ-casein glycomacropeptides having the pH value of 4 or lower with an anion exchanger; collecting by elution of a fraction which adsorbs on the anion exchanger; and concentrating and desalinating the eluted solution to obtain the κ-casein glycomacropeptide.

5 Claims, No Drawings

PROCESS FOR PRODUCING K-CASEIN GLYCOMACROPEPTIDES

BACKGROUND OF THE INVENTION

The present invention relates to a process for the simple production of κ-casein glycomacropeptides having useful physiological activities.

It is known that κ-casein glycomacropeptides are sialilated peptides which are produced from κ-casein of cow's milk by the action of proteolytic enzymes such as rennet and pepsin, and they are present in cheese whey.

Hitherto, some methods were reported for the production of κ-casein glycomacropeptides, for example, a method comprising dissolving κ-casein which is isolated from cow's milk in deionized water, reacting the obtained solution with pepsin, adding trichloroacetic acid to the solution to precipitate a para-κ-casein fraction, dialyzing the obtained supernatant against deionized water for desalting, and freeze-drying the obtained solution (Seo et al., Journal of Food Science 53, 80 (1988)); and a method comprising dissolving the above κ-casein in deionized water, adjusting the pH of the solution to 6.7, reacting the solution with rennet, readjusting the pH to 4.6 to precipitate the para-κ-casein, removing the precipitate, dialyzing the obtained supernatant for desalting, and freeze-drying the obtained solution (Published by Academic Press Company, "Milk Protein", pp 200).

However, these methods are conducted in laboratories and are not suitable for mass production.

On the other hand, since the industrial utilization of κ-casein glycomacropeptides has been previously unknown, a method for mass producing the compounds has not been studied.

Since it was reported that after taking κ-casein glycomacropeptides dogs appetite were reduced (Bulletin of Experimental Biology and Medicine, 96, 889, (1983)), it has been found that the compounds can be utilized as food materials for the prevention of obesity.

Further, since it was found that κ-casein glycomacropeptides were effective to prevent the adhesion of *E. coli* to cells of the intestines, to prevent infection of influenza virus (Japanese Patent Unexamined Publication No. 63-284133) or to protect the adhesion of tartar to teeth (Japanese Patent Unexamined Publication No. 63-233911), the demand for the production of κ-casein glycomacropeptides on a large industrial scale is expected.

Given such conditions, a process for preparing a κ-casein glycomacropeptide from rennet casein curd whey has been reported (Japanese Patent Unexamined Publication No. 63-284199). Since the reaction of the process may proceed without the trichloroacetic acid of the prior art, the process can be utilized in food fields and in massproduction. However, the method is always associated with the production of large amount of the rennet casein curds which are obtained as a by-product of the rennet casein curd whey. If the rennet casein curds are not utilized, the production cost of κ-casein glycomacropeptides becomes expensive.

The inventors of the present invention found that the molecular weight of κ-casein glycomacropeptide changes sharply at pH 4. Using the property, they found a process for producing the κ-casein glycomacropeptide at a moderate price (Japanese Patent Unexamined Publication No. 276542).

The process for the production of κ-casein glycomacropeptides comprises adjusting the pH to below 4 of a solution of milk starting materials such as cheese whey, whey protein concentrate and cheese whey from which protein has been removed, treating the solution by ultrafiltration with a membrane having a molecular weight cut-off of 10,000–50,000 to obtain the filtrate of the solution, preferably readjusting the pH of the filtrate to 4 or higher, and concentrating the obtained filtrate with a membrane having a molecular weight cut-off of 50,000 or less to obtain the desalted concentrate.

According to the above invention, the pH value of the solution of milk starting materials such as cheese whey, whey protein concentrate and cheese whey from which protein has been removed is adjusted. Such a simple operation can provide a process for producing κ-casein glycomacropeptides on a large scale and at a low cost. The obtained product has high purity.

Moreover, in a factory where the whey protein concentrates have been produced, new equipment is not required because κ-casein glycomacropeptides can be produced with the ultrafilter or the reverse osmosis hyperfilter used for preparing the whey protein concentrate. The protein fraction from which the κ-casein glycomacropeptides have been removed can be used as the whey protein concentrates.

However, to lower the production cost of κ-casein glycomacropeptides, the whey protein concentrates should be prepared by desalting and drying after neutralizing the whey proteins which are by-products in the process. Further, when the κ-casein glycomacropeptides are recovered from the whey concentrate obtained by ultrafiltration, the permeation flux is lowered by the protein fouling. As a result, the problem is the necessity of long time operation.

In addition, a method for the mass production of a κ-casein glycomacropeptide is disclosed in Japanese Patent Application No. 2-95686. The method comprises heating a solution containing whey proteins, freezing the solution, thawing the frozen solution, concentrating the obtained supernatant to obtain the desalted concentrate of the κ-casein glycomacropeptide. The cost and the operation time are improved by the method, but the purity of the κ-casein glycomacropeptide is not increased.

Furthermore, the inventors of the present invention found that the electric charge of κ-casein glycomacropeptide was highly negative in comparison with the other milk proteins. Using the property, they found a process for separating the κ-casein glycomacropeptide from the other protein admixtures by using a cation exchanger (Japanese Patent Application No. 2-325166).

In the process, a fraction produced as by-products in the process that uses a cation exchanger to produce whey protein isolates (WPI) from cheese whey as raw materials can be used as raw materials to obtain a κ-casein glycomacropeptide. It is advantageous to the cost. When the solution containing the κ-casein glycomacropeptide thus obtained is concentrated and desalinated through ultrafiltration membranes, fouling problem of whey proteins on the membranes are minimized. Since permeation flux of the filtrate is increased, the operation time is shortened in comparison with conventional methods.

SUMMARY OF THE INVENTION

Then, the inventors of the present invention earnestly investigated the physicochemical properties of κ-casein glycomacropeptides. They found that when the pH value of milk raw materials containing κ-casein glycomacropeptides was adjusted to below 4, κ-casein glycomacropeptides specifically adsorbed to an anion exchanger so that the other protein admixtures could be separated.

κ-Casein glycomacropeptides have many carboxyl groups on the surface of the molecules, such as side chains of aspartic acid, glutamic acid and sialic acid. The former groups have the pKa value of 3 to 5, and the latter groups have the pKa value of 2.7. When the pH value is 4 or lower, it is possible to separate κ-casein glycomacropeptides from the other protein admixtures by adsorbing the κ-casein glycomacropeptides on an anion exchanger because the molecules of the κ-casein glycomacropeptides contain sialic acid, which has a negative charge at pH 4 or lower, whereas other milk proteins are neutrally or positively charged at this pH because they contain very few sialic acid groups.

The present invention provides a process for producing κ-casein glycomacropeptides, characterized in that it comprises contacting milk raw materials containing a κ-casein glycomacropeptides having a pH value of 4 or lower with an anion exchanger; collecting a fraction which adsorbs on the anion exchanger by; and concentrating and desalting the eluted solution to obtain the κ-casein glycomacropeptides.

It is preferred to use a strong basic anion exchanger as an ion exchanger. Preferably, when the eluted solution is concentrated and desalinated, the pH value of the eluted solution is adjusted to below 4. Then, the eluted solution is treated by ultrafiltration with a membrane having a molecular weight cut-off of 10,000 to 50,000 to obtain a filtrate. The filtrate is concentrated and desalinated with a membrane having a molecular weight cut-off of 10,000 or less.

Pure compounds can be obtained by a process described in Japanese Patent Application No. 2-276542. Namely, the pH value of the fraction is adjusted to pH 4 or lower, the fraction is treated with a membrane having a molecular weight cut-off of 10,000 to 50,000, the pH value of the obtained filtrate is readjusted to pH 4 or higher, and the filtrate is concentrated, desalinated and dried to obtain κ-casein glycomacropeptides.

According to the process of the present invention, it is very rare to face with the fouling problem of whey proteins on the surface of the ultrafiltration membranes. Permeation flux of the filtrate is increased. As a result, κ-casein glycomacropeptides having high purity are obtained in an short time operation.

DETAILED DESCRIPTION OF THE INVENTION

The following describes in detail the process for preparing κ-casein glycomacropeptides of the present invention.

Technique for the adsorption of whey proteins on an ion exchanger has been previously known; J. N. de Wit et al., Neth. Milk Dairy J., 40, 41–56 (1986), J. S. Ayers et al., New Zealand J. Dairy Sci. and Tech., 21, 21–35 (1986), Japanese Patent Unexamined Publication No. 52-151200 and Japanese patent Unexamined Publication No. 2-104246.

Any kind of milk raw materials containing κ-casein glycomacropeptides may be used. Cheese whey, rennet casein whey, whey protein concentrates which are produced by ultrafiltration of these wheys, whey and/or rennet casein whey from which whey protein precipitates have been removed by heat treatment or the like, and lactose mother liquor may be exemplified.

When the whey protein concentrates are used, the concentrates are reconstituted with water. The concentration is not limited. Any kind of cheese whey can be used. Since small quantities of casein curds and fatty contents remain in these wheys containing the rennet casein whey, they are removed with a centrifuge, a cream separator or a clarifier prior to use. Lactose principally contained in the cheese, whey from which protein has been removed by heating, is precipitated upon cooling. In this case, the precipitated lactose is removed with a centrifuge, a clarifier or by decantation.

Then, the pH value of the raw materials is adjusted to 4 or lower. The pH adjustment can be achieved using an acid such as hydrochloric acid, sulfuric acid, acetic acid, lactic acid and citric acid. For ion exchangers, an ion exchanger having diethylaminoethyl groups or quaternary amine groups may be exemplified. A method for adsorbing whey proteins containing κ-casein glycomacropeptides on an ion-exchanger is achieved using said conventional methods and separating into a fraction containing compounds adsorbed on an ion-exchanger and a fraction containing compounds not adsorbed on the ion-exchanger. The adsorbed compounds are desorbed from the ion-exchanger by inceasing the salt concentration (more than 0.1 mol/l).

Moreover, in the step of contacting an exchanger with raw materials, a rotating column disclosed in Japanese Patent Unexamined Publication No. 2-138295 is preferably used to treat efficiently the materials in a large scale.

The desorbed fraction thus obtained may be concentrated and desalinated. The monomer of κ-casein glycomacropeptides (molecular weight 9,000) is obtained at a pH value 4 or lower and the polymer of κ-casein glycomacropeptides (molecular weight 40,000–5,000) is obtained at a pH value above 4. In the step of concentrating and desalinating a solution by ultrafiltration, when the pH value of the solution is 4 or lower, a membrane having a molecular weight cut-off of 10,000 or less should be used. Membranes with molecular weight cut-off of 10,000 to 50,000 should be used when the pH of the solution is adjusted to 4 or higher.

When highly pure κ-casein glycomacropeptides is required, the pH value of said desorbed fraction is adjusted to 4 or lower, preferably to 3±0.5. When the pH value is 4 or higher, the molecules of the κ-casein glycomacropeptide are associated, the molecular weight becomes greater and these molecules do not pass readily through the membrane. The lower limit of the pH value is not particularly limited. When the pH value is 2.5 or lower, sialic acid which is glycosidated to the κ-casein glycomacropeptide becomes unstable, so that the physiological effectiveness of the compound is lowered. However, when a κ-casein glycomacropeptide having little or no sialic acid is required, the pH value may be 2.5 or lower. The pH adjustment can be achieved using an acid such as hydrochloric acid, sulfuric acid, acetic acid, lactic acid and citric acid.

After adjusting the pH value, the solution is ultrafiltered. The molecular weight cut-off of the membrane used in the ultrafiltration step is 10,000 to 50,000. When a membrane having a molecular weight cut-off of below 10,000 is used, the molecules of the κ-casein glycomacropeptide do not readily pass through the membrane. When a membrane having a molecular weight cut-off of above 50,000 is used, the molecules of the κ-casein glycomacropeptide can pass through the membrane together with a part of the coexisting whey proteins, so that the purity of the κ-casein glycomacropeptide is decreased. Usually, in the production process of whey protein concentrates, the whey proteins are ultrafiltered with a module equipped with a membrane having a molecular weight cut-off of about 20,000. In the process of the present invention, the above membrane can be used.

In the ultrafiltration step, the solution is preferably concentrated up to the limit and thus an improved yield rate of the filtrate is achieved. It is also preferred that water is added to the concentrated solution and the ultrafiltration is conducted, repeatedly. For increasing the permeate flux of the filtrate, the solution may be heated at about 50° C. or higher. However, when the temperature is above 60° C., the whey protein is precipitated or gels, so that the solution is preferably heated at 60° C. or less. The obtained concentrate is dried after adjusting the pH value to neutral to obtain the powder of whey protein concentrates.

The filtrate obtained by a such process contains the κ-casein glycomacropeptide, lactose and mineral. Since the concentration of the κ-casein glycomacropeptide is lowered, the filtrate should be desalinated and concentrated. The two methods of desalting and concentrating are as follows.

In the first method, after adjusting the pH of the filtrate to 4 or higher, the filtrate is filtered with a membrane having a molecular weight cut-off of 50,000 or less by ultrafiltration, diafiltration or reverse osmosis hyperfiltration. The pH of the filtrate can be adjusted by an alkali such as sodium hydroxide, sodium bicarbonate and ammonia water. The monomer of the κ-casein glycomacropeptide (molecular weight 9,000) is obtained at a pH value of 4 or lower, and the polymer of the κ-casein glycomacropeptide (molecular weight 40,000–50,000) is obtained at a pH value of above 4. If desired, the pH value is adjusted to 5 or higher. Further, any membrane having a molecular weight cut-off of 50,000 or less may be used. When a membrane having a molecular weight cut-off of above 50,000 is used, the κ-casein glycomacropeptide passes through the membrane. A membrane having a molecular weight cut-off of about 20,000 which is used in the usual process of producing the whey protein concentrates can be conveniently used.

When the pH of the filtrate is not readjusted to 4 or higher, the κ-casein glycomacropeptide exists in the monomer form. Then, the second method is used. In this method, the concentrate is obtained by means of a membrane having a molecular weight cut-off of 10,000 or less, preferably 8,000 or less by ultrafiltration, diafiltration or reverse osmosis hyperfiltration.

These methods can be combined with a desalting process, e.g. by means of electrodialysis or by using an ion exchanger.

Since the obtained concentrate substantially contains only the κ-casein glycomacropeptide, it can be dried by spray drying or freeze-drying. Furthermore, since the κ-casein glycomacropeptide is stable to heat, it is preferred to add a pasteurizing or sterilizing step prior to the drying step.

As described above, according to the present invention, κ-casein glycomacropeptides can be simply produced by separating the κ-casein glycomacropeptides adsorbed on an anion exchanger from the other protein admixtures.

Further, when the process of the present invention is applied to the desalinating step of cheese whey, κ-casein glycomacropeptides can be collected from a solution obtained by washing an ion exchanger which has been used for desalting cheese whey. Accordingly, the production cost is lowered.

Since the main whey proteins have previously been removed, the decrease of permeation flux based on the fouling of whey proteins scarcely occurs and the operation time is shortened in comparison with conventional methods. Further, the products can be obtained without using additives such as trichloroacetic acid. Accordingly, the obtained κ-casein glycomacropeptides can be used as raw materials for food and medical supplies. It is very useful in industrial fields.

DESCRIPTION OF THE PREFERRED EMBODIMENTS

The following examples illustrate the present invention more specifically.

EXAMPLE 1

The pH whey of 10 kg of cheddar cheese whey was adjusted to 3.0 using hydrochloric acid. 25 g of DEAE-Sephadex A-50 (manufactured by Pharmacia Company, trade name) swelled in water at 40 ° C. was charged in a packed-bed type column. The above whey solution was passed through the column at a flow rate of 0.5 liter/hour. Then, after the column was washed with water, 10 liters of a 1M sodium chloride solution was passed through the column. The eluted solution was collected. The column was washed with 2 liters of water. 11.5 liters of the eluted solution and the wash liquid were collected. The collected solution was ultrafiltered at 50 ° C. with an ultrafiltration membrane having a molecular weight cut-off of 20,000 (manufactured by DDS Company, trade name: GR 61 pp). The concentrated solution was desalinated by diafiltration and the filtrate was freeze-dried to obtain 180 mg of κ-casein glycomacropeptide powder. The purity 51% of the powder was determined by an urea-SDS electrophoresis method.

EXAMPLE 2

Using the same method as in Example 1, 11.4 liters of a fraction which had adsorbed on DEAE-Sephadex A-50 was obtained from 10 kg of Gouda cheese whey. The pH value of the fraction was adjusted to 3.5 by using hydrochloric acid. The fraction was ultrafiltered at 50 ° C. with an ultrafiltration membrane having a molecular weight cut-off of 20,000 and 11 liters of a filtrate was obtained. A 25% sodium hydroxide solution was added to the filtrate to adjust the pH value to 7.0. The filtrate was concentrated with an ultrafiltration membrane having a molecular weight cut-off of 20,000. The concentrated solution was desalinated by a diafiltration and the filtrate was freeze-dried to obtain 77 mg of κ-casein glycomacropeptide powder. The purity 87% of the powder was determined by an urea-SDS electrophoresis method.

EXAMPLE 3

The pH value of 200 liters of rennet casein whey was adjusted to 3.0 with hydrochloric acid. The whey solution was passed through a rotary column having an internal space of 14 liters in which 5 liters of QMA (manufactured by Rhone-Poulenc S.A.) swelled in water at 50° C. was charged, at a flow rate of 1000 liters/hour for 4 hours. Then, water was passed through the column at the same flow rate for 3 minutes to wash the resin. About 230 kg of non-adsorbed whey and wash liquid were obtained. 1M NaCl solution was then passed through the rotary column at 1000 liters/hour for 5 minutes and water was passed through the column at the same flow rate for 3 minutes to collect 130 liters of adsorbed fractions. The pH value of the fractions were adjusted to 3.5, the fractions were treated with an ultra-filter having an membrane of a molecular weight cut off of 20,000 to obtain 110 liters of a filtrate. A 25% sodium hydroxide solution was added to thus obtained filtrate and the pH value of the filtrate was adjusted to 7.0. The filtrate was concentrated with an membrane of a molecular weight cut-off of 20,000, and the obtained concentrate was desalinated by diafiltration and concentrated with a rotary evaporator to obtain 130 ml of a concentrate. The concentrate was spray-dried with a Pulvis minispray-GA-31 (manufactured by Yamato Company) at an inlet temperature of 150° C. and an outlet temperature of 85° C. to obtain 19 g of κ-casein glycomacropeptide powder. The purity 81% of the powder was determined by an urea-SDS electrophoresis method.

On the other hand, the above non-adsorbed whey and wash liquid were desalinated with a rotary column having an internal space of 14 liters in which 5 liters of Vistec CM (manufactured by Viscose Group Company) under the same conditions as described above. The obtained solution was concentrated by evaporation. The concentrate was spray-dried to obtain 9.8 kg of whey powder was obtained.

We claim:

1. A process for producing κ-casein glycomacropeptides which comprises;
   adjusting a milk material containing said κ-casein glycomacropeptides to a pH of about 4 or lower;
   contacting said milk material containing κ-casein glycomacropeptides having a pH value of 4 or lower with an anion exchanger;
   collecting a fraction of said milk material to which adsorbs on the anion exchanger by elution from said anion exchanger to provide an eluted solution; and,
   concentrating and desalinating the eluted solution to obtain the κ-casein glycomacropeptides.

2. A process as claimed in claim 1, wherein the anion exchanger is a strong basic anion exchanger.

3. A process as claimed in claim 1 wherein the concentrating and desalinating step comprises:
   adjusting the pH value of the fraction adsorbed on the anion exchanger to below 4;
   ultrafiltering the fraction with a membrane capable of retaining molecules having a molecular weight above 10,000 to 50,000 to obtain a filtrate; and
   ultrafiltering the obtained filtrate with a membrane retaining molecules having a molecular weight of 50,000 or less to concentrate and desalinate the κ-casein glycomacropeptides.

4. A process as claimed in claim 3, wherein the pH value of the filtrate obtained by ultrafiltration is readjusted to pH 4 or higher.

5. A process as claimed in claim 3, wherein the membrane retaining molecules having a molecular weight of 10,000 or less is used in said step of ultrafiltering the filtrate.

* * * * *